United States Patent [19]

Balzer et al.

[11] Patent Number: 4,693,848

[45] Date of Patent: * Sep. 15, 1987

[54] PREPARATION OF ALKALI METAL AND ALKALINE EARTH METAL SALTS OF ACYLOXYBENZENESULFONIC ACIDS

[75] Inventors: Wolf-Dieter Balzer, Ludwigshafen; Hans-Heinrich Bechtolsheimer, Dittelsheim-Hessloch; Karl-Heinz Beyer, Frankenthal; Rolf Fikentscher, Ludwigshafen; Johannes Perner, Neustadt; Rudi Widder, Leimen; Helmut Wolf, Hassloch, all of Fed. Rep. of Germany

[73] Assignee: Basf Aktiengesellschaft, Ludwigshafen, Fed. Rep. of Germany

[*] Notice: The portion of the term of this patent subsequent to May 13, 2003 has been disclaimed.

[21] Appl. No.: 847,196

[22] Filed: Apr. 2, 1986

Related U.S. Application Data

[63] Continuation of Ser. No. 662,048, Oct. 18, 1984, Pat. No. 4,588,531.

[30] Foreign Application Priority Data

Oct. 19, 1983 [DE]  Fed. Rep. of Germany ....... 3337921

[51] Int. Cl.⁴ .................. C07C 143/90; C07C 79/46; C07C 69/76
[52] U.S. Cl. ..................................... 260/402; 560/20; 560/61; 560/113; 560/142
[58] Field of Search .................. 260/402; 560/20, 61, 560/113, 142

[56] References Cited

U.S. PATENT DOCUMENTS 3,503,888  3/1970  Miller et al. ..................... 252/117

FOREIGN PATENT DOCUMENTS 859451  10/1952  Fed. Rep. of Germany.

*Primary Examiner*—J. E. Evans
*Attorney, Agent, or Firm*—Oblon, Fisher, Spivak, McClelland & Maier

[57] ABSTRACT

Alkali metal and alkaline earth metal salts of acyloxybenzenesulfonic acids of the formula I

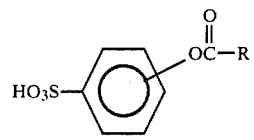

where R is a saturated or unsaturated alkyl radical of 1 to 17 carbon atoms or is phenyl which is unsubstituted or monosubstituted or disubstituted by alkyl of 1 to 3 carbon atoms, halogen, methoxy or nitro, are prepared by neutralization, by a method in which a liquid acyloxybenzenesulfonic acid of the formula I and an aqueous solution of an alkali metal or alkaline earth metal hydroxide, carbonate or bicarbonate are combined in water, at from 0° to 60° C. and while mixing thoroughly, so that the pH is kept at from 2.5 to 7.0, and, if desired, the resulting salt is isolated from the aqueous solution in a conventional manner.

6 Claims, No Drawings

PREPARATION OF ALKALI METAL AND ALKALINE EARTH METAL SALTS OF ACYLOXYBENZENESULFONIC ACIDS

This is a continuation of application Ser. No. 662,048, filed Oct. 18, 1984, now U.S. Pat. No. 4,588,531.

The present invention relates to the preparation of alkali metal and alkaline earth metal salts of acyloxybenzenesulfonic acids by neutralization. These salts are particularly useful as acylating agents in aqueous media or as detergent components.

It is known that acyloxybenzenesulfonic acids, in the form of activated esters, are acylating agents for amines, mercaptans, hydrogen peroxide and other compounds containing active hydrogen. For some applications, such as the acylation of solids or of water-insoluble polymeric compounds and for use as cold bleach activators in detergents, for example as described in European Patent Application No. 28,432, British Pat. No. 864,798 or German Laid-Open Application DOS No. 2,602,510, it is advantageous if the acylating agents are water-soluble. Examples of such water-soluble acylating agents are the salts of acyloxybenzenesulfonic acids, such as the known p-benzoyl oxy- or p-acetoxybenzene sulfonates. The use of salts of acyloxybenzenesulfonic acids in toilet soaps has also been disclosed, for example in U.S. Pat. No. 3,503,888.

The acyloxybenzenesulfonates can be prepared directly or in suspended form in an inert organic medium, for example by reacting sodium phenolsulfonate with an acid chloride or anhydride. As a rule, this reaction takes place very slowly since the reactants and/or the products do not form a homogeneous phase. To obtain yields which are at all advantageous, it is necessary to employ an excess of acylating agent and to carry out the reaction at elevated temperatures, as described in, for example, German Laid-Open Application DOS No. 2,602,510.

Another disadvantage of this process is that the sodium salt of the phenolsulfonic acid being esterified crystallizes with water of crystallization, and is obtainable virtually only in this form. Dehydration of the sodium phenolsulfonate under conventional industrial conditions, eg. heating under reduced pressure or azeotropic dehydration, is complicated and expensive and may result in discoloration. If the hydrated sodium phenolsulfonate is acylated with a carboxylic acid chloride, the water of crystallization may result in the formation of a relatively large amount of an acid which is difficult to separate off.

It is known that the abovementioned activated phenol esters are very sensitive to hydrolysis, substantial hydrolysis occurring after a short time in water at as low as room temperature. Even at a pH above 7.5, ie. in the alkaline range, hydrolysis takes place very rapidly, as is evident from, for example, U.S. Pat. No. 3,503,888, column 4, line 3 et seq. For this reason, it is very difficult to prepare the alkali metal and alkaline earth metal salts of acyloxybenzenesulfonic acids without loss as a result of hydrolysis reactions. Attempts to convert the anhydrous acyloxybenzenesulfonic acids in an inert organic solvent, such as dioxane, acetone or a chlorohydrocarbon, with, for example, an alkali metal carbonate, bicarbonate or acetate, to give salts were also unsuccessful. Protic solvents, in particular lower alcohols or glycols, cannot be used as solvents since they result in transesterification. Thus, the salts of the most frequently used acyloxybenzenesulfonic acids are difficult to obtain in pure form.

It is an object of the present invention to provide a process for the preparation of alkali metal and alkaline earth metal salts of acyloxybenzenesulfonic acids by neutralization in an aqueous medium, the process being easy to carry out industrially on a large scale and giving very pure salts which are not discolored and are suitable for use in practice.

We have found that this object is achieved by a process for the preparation of alkali metal and alkaline earth metal salts of acyloxybenzenesulfonic acids of the formula I

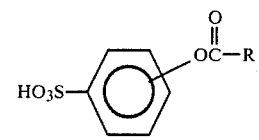

where R is a saturated or unsaturated alkyl radical of 1 to 17 carbon atoms or is phenyl which is unsubstituted or monosubstituted or disubstituted by alkyl of 1 to 3 carbon atoms, halogen, methoxy or nitro, by neutralization, wherein a liquid acyloxybenzenesulfonic acid of the formula (I) and an aqueous solution of an alkali metal or alkaline earth metal hydroxide, carbonate or bicarbonate are combined in water, at from 0° to 60° C. and while mixing thoroughly, so that the pH is kept at from 2.5 to 7.0, and, if desired, the resulting salt is isolated from the aqueous solution in a conventional manner.

Suitable radicals R are saturated or unsaturated, straight-chain or branched alkyl radicals of 1 to 17, preferably 5 to 17, carbon atoms. Specific examples are methyl, ethyl, pentyl, n-heptyl, 2-ethylpentyl, 2-ethylhexyl, n-octyl, branched octyl radicals 3,5,5-trimethylpentyl, n-nonyl, 3,5,5-trimethylhexyl, undecyl, heptadecyl and heptadecenyl.

Examples of substituted phenyl radicals R are tolyl, anisyl and chlorophenyl.

Furthermore, the radical —O—COR is preferably in the p-position in the formula (1).

The acyloxybenzenesulfonic acids of the formula (I) are prepared in a conventional manner, as described in, for example, U.S. Pat. No. 3,503,888.

Under the special conditions in the process according to the invention, acyloxybenzenesulfonic acids can be neutralized in an aqueous medium without any significant hydrolysis, in a manner which could not be foreseen. An advantageous procedure is as follows: the liquid acyloxybenzenesulfonic acid and a 5-50% strength by weight aqueous solution of the alkali metal or alkaline earth metal hydroxide, carbonate or bicarbonate are run simultaneously into water, at from 0° to 60° C., preferably from 10° to 40° C., while stirring, so that a pH of from 2.5 to 7.0, preferably from 3.0 to 5.5, is maintained.

The neutralization can be carried out batchwise or continuously. In the continuous procedure, the components water, acyloxybenzenesulfonic acid and alkali are combined in a static or dynamic mixer.

It should be pointed out that a substantial amount of heat is generated when the acyloxybenzenesulfonic acids dissolve in water. In addition to this, there is the heat of neutralization. This total amount of heat must be removed by cooling. Hence, in the industrial procedure of the neutralization according to the invention, as a rule from 3 to 10 hours are required, depending on the amount of acyloxybenzenesulfonic acid being neutralized. If the neutralization is carried out by a continuous procedure, a heat exchanger of appropriate dimensions is required downstream from the mixer.

Using the novel process, it is possible to prepare stable aqueous solutions of the acyloxybenzene sulfonates in concentrations of from 20 to 60% by weight. The pure salts can be isolated from these solutions in a conventional manner, for example by evaporation, spray drying, freeze drying, drum drying or drying in a fluidized bed.

In a particularly preferred embodiment, the neutralization according to the invention is carried out in the presence of from 1 to 2% by weight, based on the acyloxybenzenesulfonic acid, of a water-soluble phosphate, phosphite or tartrate, of a complexing agent for heavy metals, or of a polymer of acrylic acid and maleic acid. As a rule, the water-soluble sodium salts are used in this procedure.

If the sodium acyloxybenzenesulfonates obtained by spray drying are dissolved in water, yellow or slightly brownish solutions are obtained which may darken on exposure to light. Surprisingly, we have found that these solutions possess substantially less color, and have a smaller tendency to become decolorized during further processing, if the neutralization is carried out in the presence of the above compounds. Examples of effective substances of this type are sodium dihydrogen phosphate, disodium tartrate, sodium hydrogen tartrate, sodium phosphite, hypophosphorous acid, nitrilotriacetic acid, ethylenediaminetetraacetic acid, diethylenetriaminepentaacetic acid, hydroxyethylethylenediaminetriacetic acid, nitrilotrimethylenephosphonic acid and polycarboxylic acids obtained from acrylic acid and/or maleic acid, and their Na salts.

EXAMPLE 1

100 parts of an acryloxybenzenesulfonic acid of the formula I were run into 100 parts of water, while stirring thoroughly. At the same time, 50% strength by weight aqueous sodium hydroxide solution was added dropwise so that the pH of the aqueous solution was from 3.0 to 5.5 (monitored by means of a glass electrode). The reaction mixture was kept at below 50° C. by cooling. When the addition of the acyloxybenzenesulfonic acid was complete, the solution was brought to pH 5.5, and the sodium salt was isolated from the aqueous solution by spray drying.

To assess the color of the resulting sodium salt, the iodine color number according to DIN 53403 was determined for a 50% strength by weight aqueous solution.

EXAMPLE 2

100 parts of water, 100 parts of acyloxybenzenesulfonic acid and 50% strength by weight aqueous sodium hydroxide solution were run simultaneously into a flask, while mixing thoroughly with a stirrer. The feed of the sodium hydroxide solution was controlled so that the pH was kept constantly at 5.5. The reaction mixture was kept at below 50° C. by cooling. The resulting sodium salt of the acyloxybenzenesulfonic acid was isolated from the aqueous solution by spray drying.

EXAMPLE 3

The procedure described in Example 1 was followed, except that 1% by weight of sodium dihydrogen phosphate was added to the water initially taken. Spray drying gave a sodium salt whose color was substantially paler than that of a sodium salt obtained in the absence of sodium dihydrogen phosphate.

EXAMPLE 4

The same result as in Example 3 was obtained when 1% by weight of sodium dihydrogen phosphate was added to the water in a continuous procedure described in Example 2.

Using these general methods, the sodium salts of 2-ethylhexanoly-, n-octanoyl-, isononanoyl- (=3,5,5-trimethylhexanoyl-), oleoyl- and stearoyloxybenzenesulfonic acid were prepared.

EXAMPLE 5

100 parts of isononanoyloxybenzenesulfonic acid were run into 100 parts of water. At the same time, 50% strength by weight aqueous sodium hydroxide solution was added dropwise so that the pH was kept at 4.0. The reaction mixture was maintained at 40° C., and the solution was stirred for a total of 5 hours at this temperature, after which the pH was brought to 5.5 with 50% strength by weight aqueous sodium hydroxide solution. The sodium salt was isolated from the solution by spray drying.

COMPARATIVE EXAMPLE A 100 parts of isononanoyloxybenzenesulfonic acid were run into 100 parts of water. At the same time, 50% strength by weight aqueous sodium hydroxide solution was added dropwise so that the pH was kept at 2.0. The reaction mixture was maintained at 40° C., and the solution was stirred for a total of 5 hours at this temperature, after which the pH was brought to 5.5 with 50% strength by weight aqueous sodium hydroxide solution. The sodium salt was isolated from the solution by spray drying.

COMPARATIVE EXAMPLE B

The procedure described in A was followed, except that the pH was maintained at 7.5.

COMPARATIVE EXAMPLE C

The procedure described in A was followed, except that the pH was maintained at 8.0.

TABLE 1

| Example | pH during the 5-hour stirring period | Content of acyloxybenzenesulfonate in %, based on Example 5 (two-phase titration according to Epton) |
| --- | --- | --- |
| 5 | 4.0 | 100 |
| A | 2.0 | 68.3 |
| B | 7.5 | 92.1 |
| C | 8.0 | 91.0 |

The stated ester content, which is set at 100% for a salt prepared according to the invention (Example 5), indicates a relative decrease in content. In fact, about 1-2% of the acyl compound was hydrolyzed in the procedure according to the invention.

The Table shows that hydrolysis of the acyloxybenzenesulfonate increases at a pH which is lower or higher than the pH according to the invention.

TABLE 2

| Iodine color numbers according to DIN 53403 Preparation of sodium isononanoyloxybenzene sulfonate, with the addition of 1% by weight of . . . | Iodine color number (DIN 53403) of a 50% strength (w/w) solution |
|---|---|
| no additive | 30 |
| sodium dihydrogen phosphate | 10 |
| disodium tartrate | 10 |
| sodium hydrogen tartrate | 10 |
| hypophosphorous acid | 10 |
| trisodium polyphosphate | 15 |
| nitrilotriacetic acid | 15 |
| ethylenediaminetetraacetic acid | 15 |
| diethylenetriaminepentaacetic acid | 10 |
| hydroxyethylethylenediaminetriacetic acid | 10 |
| acrylic acid/maleic acid copolymer | 10 |
| nitrilomethylenephosphonic acid | 10 |

We claim:

1. A process for the preparation of an alkali metal or alkaline earth metal salt of an acyloxybenzenesulfonic acid of formula I:

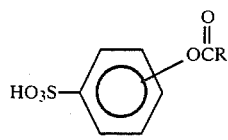

wherein R is a saturated or unsaturated alkyl radical of 1 to 17 carbon atoms, phenyl or phenyl monosubstituted or disubstituted by an alkyl radical of 1 to 3 carbon atoms, halogen, methoxy or nitro, comprising:
simultaneously adding liquid acyloxybenzenesulfonic acid and a 5–50% strength by weight aqueous solution of an alkali metal or alkaline earth metal hydroxide, carbonate or bicarbonate into water at a temperature of from 0° to 60° C.; and mixing the added ingredients during the addition process such that the acyloxybenzenesulfonic acid is neutralized with the pH of the water medium being maintained from 3.0 to 5.5, thereby forming an aqueous solution having an acyloxybenzenesulfonate salt concentration of 20–60% by weight.

2. The process as claimed in claim 1, wherein the neutralization is carried out in the presence of from 1 to 2% by weight, based on the acyloxybenzenesulfonic acid, of a soluble phosphate, phosphite or tartrate, of a complexing agent for heavy metal salts, or of a polymer of acrylic acid and/or maleic acid.

3. The process of claimed in claim 1, wherein the product acyloxybenzenesulfonate salt is isolated from the aqueous solution.

4. The process as claimed in claim 1, wherein the neutralization process takes from 3 to 10 hours.

5. A process for the preparation of an alkali metal or alkaline earth metal salt of acyloxybenzenesulfonic acid of formula I:

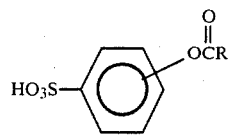

wherein R is a saturated or unsaturated alkyl radical of 1 to 17 carbon atoms, phenyl or phenyl monosubstituted or disubstituted by an alkyl radical of 1 to 3 carbon atoms, halogen, methoxy or nitro, comprising:
simultaneously adding liquid acyloxybenzenesulfonic acid and a 5–50% strength by weight aqueous solution of an alkali metal or alkaline earth metal hydroxide into water at a temperature of from 0° to 60° C.; and
mixing the added ingredients during the addition process such that the acyloxybenzenesulfonic acid is neutralized with the pH of the water medium being maintained from 3.0 to 5.5, thereby forming an aqueous solution having an acyloxybenzenesulfonate salt concentration of 20–60% by weight.

6. The process as claimed in claim 5, wherein the neutralization is carried out at from 10° to 40° C.

* * * * *